United States Patent [19]
Korfiatis et al.

[11] Patent Number: 5,629,199
[45] Date of Patent: May 13, 1997

[54] SONICALLY ENHANCED METHOD FOR REMOVING CHEMICAL PRESERVATIVES FROM CHEMICALLY TREATED WOOD PRODUCTS

[75] Inventors: George Korfiatis, Basking Ridge; Nirupam Pal, Kearny, both of N.J.

[73] Assignee: Trustees of Stevens Institute of Technology, Hoboken, N.J.

[21] Appl. No.: 617,982

[22] Filed: Mar. 15, 1996

Related U.S. Application Data

[63] Continuation of Ser. No. 340,194, Nov. 15, 1994, abandoned.

[51] Int. Cl.$^6$ ..................................................... B09B 3/00
[52] U.S. Cl. .................................... 435/262.5; 588/207
[58] Field of Search ................................ 435/262, 262.5, 435/264, 177; 588/207

[56] References Cited

U.S. PATENT DOCUMENTS

| | | | |
|---|---|---|---|
| 4,729,832 | 3/1988 | Leonard et al. | 210/639 |
| 4,734,138 | 3/1988 | Ely et al. | 134/27 |
| 5,262,004 | 11/1993 | Gilbert et al. | 162/22 |
| 5,342,779 | 8/1994 | Matsumura | 435/262.5 |

OTHER PUBLICATIONS

Portier, R., Recovery of Wood Fiber From Treated . . . Microterra Inc. Field Pilot Studies, Boca Raton FL 1–15 (1993).

Venkatadri, R., Use of a Biofilm Membrane Reactor . . . Haz Waste & Haz Mater vol. 9 No. 3 1992 pp. 231–243.

Petrier, C., Characteristics of Pentachlorophenate . . . Environ Sci Technol vol. 26 No. 8 1992 pp. 1639–1642.

Kelso W., Use of Ultrasonic Energy for Extraction . . . American Wood Preservers Assoc. vol. 70 1994 pp. 317–325.

Portier et al., "Recovery of Wood fiber from Treated Wood Products by Combined Physical, Chemical and Biological Approaches: Field Pilot Studies", Microterra, Inc., Boca Raton, FL. (1993) pp. 1–15.

*Primary Examiner*—Ralph Gitomer
*Attorney, Agent, or Firm*—Law Offices of Jane Massey Licata

[57] ABSTRACT

A method for removing chemical preservatives from wood treated with chemical preservatives is provided. Wood treated with chemical preservatives is chipped to produce wood chips. These wood chips are contacted with an organic solvent and sonicated to extract the chemical preservatives. A system for the removal of chemical preservatives from wood treated with these preservatives which contains an extraction system for contacting wood chips from wood treated with a chemical preservative with an organic solvent and a sonicator for sonicating these wood chips in the organic solvent are also provided.

2 Claims, 1 Drawing Sheet

SONICALLY ENHANCED METHOD FOR REMOVING CHEMICAL PRESERVATIVES FROM CHEMICALLY TREATED WOOD PRODUCTS

This is a continuation of application Ser. No. 08/340,194, filed Nov. 15, 1994 now abandoned.

FIELD OF THE INVENTION

The present invention provides methods and systems for the effective and quick removal of chemical preservatives such as pentachlorophenol, creosote or a mixture thereof from chemically treated wood products for environmentally safe recycling. Such recycled wood is useful for the fabrication of wood board, partition board and plywood. The recycled wood can also be used in the manufacture of paper and production of heating oil or for the production of electric power.

BACKGROUND OF THE INVENTION

Two major wood preservatives, pentachlorophenol (PCP) and creosote, have been used to prepare wood for industrial applications. For example, PCP mixed with creosote and other hydrocarbons is used to treat utility poles as well as wooden packaging boxes as an herbicide, fungicide, pesticide and biocide. The average life of these utility poles is 20-35 years, after which they are discarded. Until now, wooden poles and railroad ties were disposed of in landfills or burned in power generation plants. However, due to reported carcinogenicity of PCP, in May of 1992 the Environmental Protection Agency proposed a substantial revision to their Hazardous Waste Identification System which would lower the hazardous waste level of PCP from 100 mg/kg dry wood to 0.1 mg/kg dry wood. If this level is adopted, disposal of PCP treated wood in landfills would be prohibited. In addition, the transportation cost and cost associated with complying with clean air requirements exceeds the BTU value of wood, thus making burning of this wood to generate power uneconomical. Therefore, environmentally safe methods of recycling these materials are greatly desired.

Many prior art approaches for removing creosote deposits utilize toxic petroleum distillates or other volatile agents which require great care in handling and application. Still other problems are associated with such compositions because they are generally non-biodegradable and often may not be completely removed without the introduction of another solvent.

U.S. Pat. No. 4,734,138 (Ely et al.) discloses methods for removing creosote deposits from wood using a biodegradable "wood restorative" composition consisting of water, sodium hydroxide, sodium bicarbonate, ethylene glycol, glycerol and corn starch. This composition can be applied to creosote-treated wood and allowed to dry and then removed by conventional cleaning methods. However, this method removes only surface deposits and would not render the wood recyclable.

U.S. Pat. No. 4,729,832 (Leonard et al.) teaches methods for reducing concentrations of phenol and naphthalene contaminants in a waste water stream recovered from a wood drying process where creosote is used. A cationic organic polyelectrolyte demulsifying agent and a coal tar based extractant are used in this process. The extractant phase is then returned to the wood preserving process for further use.

U.S. Pat. No. 5,262,004 (Gilbert et al.) discloses a method for extracting chemical preservatives from wood impregnated with PCP and/or creosote. The wood is shredded to produce wood chips which are then impregnated with an aqueous solution containing an alkali hydroxide. The chips are then crushed until most of the chemical preservatives are removed. The remaining wood particles and aqueous phase which contains the chemical preservatives are discarded.

Portier et al., "Recovery of Wood Fiber from Treated Wood Products by Combined Physical Chemical and Biological Approaches: Field Pilot Studies", Microterra, Inc., Boca Raton, Fla. (1993) describe a process for the recovery of wood fiber from products which have been chemically treated with PCP or creosote. In this method both the wood fiber and wood preservative can be recycled. In an initial chipping phase, the wood is shredded and splintered to increase the wood surface area prior to chemical pretreatment. The chips are then introduced into a contact reactor where alcohol extraction occurs for about fifteen minutes. The resulting alcohol/creosote and/or PCP liquor is then distilled and the distillate recycled. The treated wood chips are then inoculated with flavobacterium and acinetobacter species to polish any residual PCP and/or creosote from the wood. The treatment results in approximately 98.7% of the PCP being removed after 21 days at an approximate cost of $160.00/ton. Others have reported that the process takes three months and costs approximately $200/ton. Such long treatment makes this process undesirable for commercial use. In addition, the PCP content in utility poles has been found to be as high as 20,000 mg/kg of wood. Thus, remaining PCP in wood following treatment with this process is around 325 mg/kg of wood rendering the wood unusable for reuse in fiberboard or in paper manufacture. Careful control of environmental variables such as bacterial seeding, pH, oxygen concentration, aeration and temperature during the polishing step has been reported to increase mineralization of creosote and PCP to greater than 99.99% using this process.

There remains a need for rapid and efficient methods and systems for the removal of chemical preservatives such as PCP, creosote and/or mixtures thereof from wood products. There also remains a need for improved methods and systems which render treated wood products recyclable and useful. Accordingly, the method and system of the present invention, which removes virtually all of the chemical preservatives and allows both the wood and the preservative to be recycled, is highly desirable.

SUMMARY OF THE INVENTION

An object of the present invention is to provide a method for the treatment of chemically treated wood for the purpose of recycling. Chemical preservatives such as pentachlorophenol (PCP) and creosote or mixtures thereof are used to treat a variety of wood products including, but not limited to, utility telephone poles, utility electrical poles, railroad ties and wooden boxes. These preservatives can constitute up to 3% of the wood by weight. These chemical preservatives are hazardous chemicals and are oftentimes toxic in nature. Due to the presence of these chemicals, after normal use, such treated wood products cannot be recycled. In the present invention, treatment methods for safe recycling of this wood are provided. In accordance with the method of the present invention, wood chips from wood treated with a chemical preservative are contacted with an organic solvent and sonicated to extract the chemical preservative. Using this sonically enhanced technique, more than 99.5% of the chemical preservative can be removed in about 10 hours.

Another object of the present invention is to provide a system for removing a chemical preservative from wood treated with chemical preservatives. The system comprises an extraction system for contacting wood chips from wood treated with chemical preservatives with an organic solvent and a means for sonicating the wood chips with the organic solvent.

DETAILED DESCRIPTION OF THE INVENTION

Figure 1:
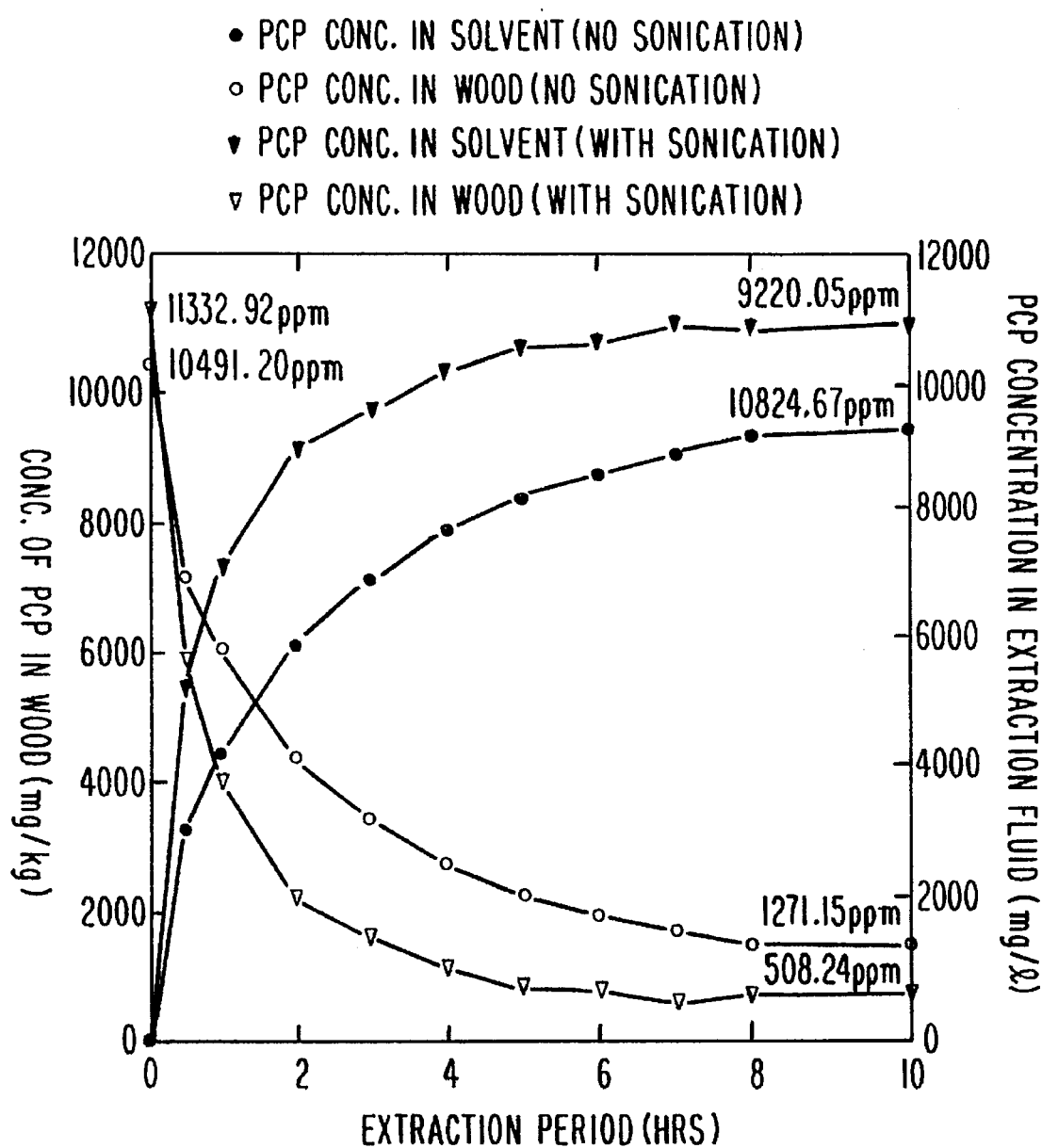
FIG. 1 is a graph showing the effect of sonication on extraction, as compared with extraction without sonication.

A variety of chemical preservatives, including but not limited to, pentachlorophenol (PCP), creosote and a mixture thereof, are used to treat many wood products including utility poles and railroad ties. Approximately 60% of all such poles and ties in service are treated with PCP. This treatment renders these woods immune to microbial or pestal attack. The lifetime of the poles and ties is normally 20 to 35 years, after which time they are discarded. Approximately 2.5 million utility poles and 10 to 15 million railroad ties are discarded every year. Due to the presence of chemical preservatives such as PCP and/or creosote in these discarded poles and ties, disposal in landfills is becoming difficult. In the present invention, a treatment technology is described which can render treated wood free from chemicals such as PCP, creosote, or mixtures thereof. The method of the invention, which employs sonication to enhance the removal of the chemical preservatives from the wood, is effective for removing virtually all of the chemical preservatives from the wood. Use of this technology, which renders contaminated wood reusable within 5 days would save more than 450 million cubic feet of wood annually in the United States alone, thus reducing the need for significant deforestation.

In accordance with the method of the present invention, the chemically treated wood is chipped into small pieces, preferably from about ⅛ inch to about ¼ inch. This can be achieved in a number of ways including, for example, passing the poles through a commercial wood chipper. Any sawdusts produced in this process are not separated but rather are processed with the chipped woods. Thus, use of the term "wood chips" in the present invention is meant to include any sawdusts produced during the chipping process.

In the next step, chemical preservatives, for example PCP creosote or a mixture thereof, are extracted from the wood chips with an organic solvent, preferably methanol, ethanol or acetonitrile, more preferably commercial grade ethanol, at approximately 35° C. Wood chips from wood treated with a chemical preservative are contacted with an organic solvent in an extraction system. In this extraction process, about 94-96% of the PCP (initial PCP concentration=12,000 mg/kg to 15,000 mg/kg) in the wood is extracted in about 10 to 12 hours. The total removal can be increased by successive extraction stages.

It was surprisingly found that this extraction time can be reduced drastically by performing the extraction under the influence of ultrasound waves. The effect of sonication on the extraction of PCP is compared with the extractions without sonication in FIG. 1. Using sonication, about 94-96% of the PCP can be removed from the wood within 2-3 hours at 35° C. in the first stage of extractions. Approximately 99.5% of the PCP can be extracted in 10 to 12 hours. By this process, PCP concentrations in the wood can be brought down to 10-50 mg/kg of wood starting from an initial concentration of 12,000 mg/kg of wood. All of the experiments performed with the present invention were done under a constant sonication intensity. However, as will be obvious to those of skill in the art upon this disclosure, variations in the sonication intensity will increase or decrease the extraction efficiency, thus resulting in changes in the extraction time.

A system for the removal of a chemical preservative such as PCP, creosote or a mixture thereof is also provided. In one embodiment, the system comprises an extraction system for contacting wood chips with an organic solvent and a means for sonicating the wood chips in the organic solvent. A means for sonicating the wood chips and organic solvent can be applied in various forms. For example, in one embodiment sonicators can be placed on the sides of an extraction system. In another embodiment, the sonicator is a movable unit which aids in the sonication step by eliminating dead zones within the extraction system.

In one embodiment, the extraction is performed in an extraction system referred to as a pipeline system. In this embodiment, the sonicators are placed outside a pipe and the wood chips mixed with the organic solvent are passed through the pipe. During the flow, the wood-solvent slurry comes under the influence of sonication and the extraction of chemical preservatives from the wood is accomplished.

In another embodiment, the extraction is performed in an extraction system referred to as a counter current system. This system, which comprises at least three tanks, has been found to increase the extraction efficiency while reducing the solvent requirement. In this extraction procedure, the wood chips are introduced into a first tank, tank 1, while fresh solvent is introduced into a third tank, tank 3. The wood from tank 1 is transferred to a second tank, tank 2, and then on to tank 3. Similarly, solvent from tank 3 is transferred to tank 2 and then to tank 1. The wood chips from tank 3 are removed for further treatment. The solvent from tank 1 is removed for regeneration. This system is easily automated with conveyors and pumps for industrial applications.

In a preferred embodiment, following the extraction step, the remaining contaminated wood is treated in a bioreactor for final detoxification. This step is referred to as the polishing step. In this step, the wood chips are separated from the solvent, preferably by passing the mixture through a metal or polymeric fabric strainer. The wood chips are then dried and placed in a bioreactor. Thus, in a preferred embodiment, a system for the removal of chemical preservatives from wood further comprises a bioreactor. The bioreactor is inoculated with a suitable microbial culture, preferably a wood rotting fungi or bacteria, more preferably *Phanerochaete chrysosporium*. The use of bioreactors is well understood by those of skill in the art. In the present invention, the bioreactor used in the method and in the system can have various configurations including, but not limited to, a slurry reactor configuration, a packed-bed configuration, a batch reactor configuration, a silo type configuration, and a combination of slurry reactor and immobilized packed-bed reactor configuration. In the slurry reactor configuration, wood chips are kept in a water-wood chips-slurry form and the system is maintained in suspension by introduction of air from the bottom of the reactor. In the silo type configuration, after separation of the wood chips from the alcohol solution, the wood chips are placed in a reactor shaped like a silo. The nutrients are dripped from the top of the reactor and the air is introduced from the bottom of the reactor. This process requires no agitation and biodegradation is achieved in the process.

In experiments, wherein a batch reactor was utilized, PCP was degraded to below 0.01 mg/kg of dry wood in 10 days.

In other experiments, wherein a continuous reactor was utilized, PCP was degraded to below 0.01 mg/kg of dry wood in 5 days. In this embodiment, following extraction, wood chips are fed into a slurry reactor in batch mode and the nutrients are introduced from the bottom of the reactor in a continuous mode. The wood chips are then fluidized via air current or agitation. Nutrients from the slurry reactor are then passed to a packed-bed reactor. In this reactor, the fungus *Phanerochaete chrysosporium* is grown and immobilized over polyesterterephthalate flakes. These microorganisms grow on the wood chips as well as in the suspension. Any PCP carried out with the nutrient mixture is completely degraded in the packed-bed reactor, and preservative free liquid comes out from the packed bed.

The organic solvent-chemical preservative extract solution produced by contacting the organic solvent with the wood chips can then be separated, preferably via distillation or membrane based separation technologies. For example, 95% of the organic solvent is regenerated by distillation and 95±5% of the PCP can be recovered as the residue in this process. For PCP, it is preferred that the distillation operation be carried out at 78° C. Examples of membrane based separation technologies which can be used to separate the organic solvent-chemical preservative extract solution include, but are not limited to, thermopervaporation, ultrafiltration and nanofiltration. Thermopervaporation is widely used commercially for separation of ethanol and other alcohol(s) from water and other solutes. The pervaporation process is a separation process in which a liquid mixture is contacted with one side of a membrane and one component permeates more quickly than the other due to vapor pressure. Differences in partial vapor pressure may be controlled by change in temperature, thus the name thermopervaporation. Ultrafiltration is primarily a size exclusion based, pressure driven, membrane separation process. Ultrafiltration is universally used for separation of salts from various organic compounds. Since the organic solvent and chemical preservatives in the extract differ considerably in their molecular size, ultrafiltration may be an extremely efficient technique for separation.

The invention is further illustrated by the following, non-limiting examples.

EXAMPLES

Example 1

Sonically Enhanced Chemical Extraction of PCP

Discarded utility poles, 15 to 20 years in age, were chipped into small pieces ranging from approximately ⅛ to ¼ inch. Approximately 50 grams of the wood chips were placed in a 2.5 liter round bottom flask. One liter of commercial grade ethanol was placed in the flask and closed in an air tight manner with a rubber stopper. The flask was then placed in a combined water bath-solid state sonicator (Fisher Scientific Model # FS-14, Pittsburg, Pa.) system, and the sonically enhanced extraction was started. The temperature of the water bath was maintained at 35° C. Liquid and wood samples were removed at predetermined intervals for analysis. The results of these experiments in comparison with extraction alone are shown in FIG. 1. Under the influence of sonication, about 90 to 96% of the PCP was removed within 2 to 3 hours of a single step extraction operation. In this study, about 99.5% of the PCP was extracted within 10 hours in three stages of extraction wherein the extraction was performed 3 times sequentially in a batch reactor with fresh ethanol each time.

Example 2

Biodegradation in a Batch Reactor

Following the extraction described in Example 1, the wood chips were separated from the solvent solution by passing the mixture through a metal or polymeric fabric strainer. The wood chips were introduced into the batch reactor along with 5 ml of an inoculum of pregrown fungal culture of *P. chrysosporium*. Nutrient media, containing glucose (0.5–0.9 g), $KH_2PO_4$ (2.0 g), $NaNO_3$ (0.02–0.04 g), $MgSO_4$ (0.5 g), thiamine hydrochloride (5 mg), and mineral salt solution (5 ml) in 1 liter of deionized water was also introduced. The mineral salt solution in the nutrient media contains $MgSO_4,7H_2O$ (3g), $MnSO_4, H_2O$ (0.5 g) , NaCl (1 g), $FeSO_4,7H_2O$ (100 mg), $CoSO_4$ (100 mg), $CaCl_2$ (2 mg), $ZnSO_4$ (100 mg), $CuSO_4,5H_2O$ (10 mg), $H_3BO_3$ (10 mg), $NaMO_4$ (10 mg) and $AlK(SO_4)$ in 1 liter of deionized water. Both wood as well as liquid from the batch reactor were periodically analyzed for PCP or any other organic compounds that may be present. PCP was degraded to below 0.01 mg/kg dry wood in 10 days. No peaks of other compounds, not normally found in untreated wood, were observed during HPLC or GC/MS analysis of the treated wood from the bioreactor. After 10 days, HPLC and GC/MS analysis of the liquid from the batch reactor showed no PCP or any other organic products.

The concentration of PCP in the extract solution was determined by reverse phase HPLC. The analyses was performed on a Varian 9010 HPLC (Palo Alto, Calif.) equipped with a diode array detector (Polychrom 9065), a solvent delivery system and an autosampler. Samples were separated on an Econosphere C-18 (5 micron) column (Alltech Associates, Deerfield, Ill.) using acetonitrile and water containing 1% glacial acetic acid in the ratio of 75:25 as the mobile phase. The flowrate was 1 ml/min. The samples were monitored at 293 nm and any peaks were quantified with the diode array detector.

For analysis of sample by GCMS, a Varian GCMS (Saturn II), in conjunction with a Varian GC 3400 was used. Helium was used as the carrier gas. Peaks were detected by ion trapping.

Example 3

Biodegradation in Continuous Reactor System

Following the extraction as described in Example 1, wood chips are fed into a slurry reactor in batch mode. Nutrients are introduced from the bottom of the reactor in a continuous mode. Air is sparged to aerate the system from the bottom. The liquid from the slurry is then passed to a next immobilized bed reactor. In this reactor, the fungus *P. chrysosporium* is grown and immobilized over polyesterterephthalate flakes as described in the prior art. Any PCP carried out with the liquid mixture coming out of the slurry reactor is completely degraded in this packed-bed reactor and PCP/creosote free liquid comes out of the packed bed.

Example 4

Separation of PCP from Extraction Solvent

The spent organic solvent or solvents generated from the various stages of extraction, as well as PCP was efficiently separated by distillation. Since the boiling point of ethanol is much lower than that of PCP, boiling the mixture results in the evaporation and separation of ethanol from the PCP. Ninety-five percent of the ethanol was separated from the PCP-ethanol extract with more than 99% purity. Approximately 99% of the PCP was also recovered from the solvent PCP mixture

What is claimed is:

1. A method for removing approximately 99.5% of pentachlorophenol, creosote or a mixture of pentachlorophenol and creosote from wood treated with pentachlorophenol, creosote or a mixture of pentachlorophenol and creosote in about 10 hours comprising:

(a) contacting wood chips from wood treated with pentachlorophenol, creosote or a mixture of pentachlorophenol and creosote with a solvent selected from the group consisting of ethanol, acetonitrile and methanol; and (b) sonicating the wood chips and solvent to extract approximately 99.5% of the pentachlorophenol, creosote or a mixture of pentachlorophenol and creosote from the wood in about 10 hours.

2. The method of claim 1 wherein concentrations of pentachlorophenol in the wood are decreased to 10–50 milligrams of pentachlorophenol per kilogram of wood from an initial concentration of 12,000 milligrams of pentachlorophenol per kilogram of wood.

* * * * *